US006150423A

United States Patent [19]
Carpenter

[11] Patent Number: 6,150,423
[45] Date of Patent: Nov. 21, 2000

[54] PROPOFOL-BASED ANESTHETIC AND METHOD OF MAKING SAME

[75] Inventor: John R. Carpenter, Savannah, Mo.

[73] Assignee: Phoenix Scientific, Inc., St. Joseph, Mo.

[21] Appl. No.: 09/173,013

[22] Filed: Oct. 15, 1998

[51] Int. Cl.[7] .................................................. A61K 31/05
[52] U.S. Cl. .......................................... 514/731; 514/816
[58] Field of Search ...................................... 514/816, 731

[56] References Cited

U.S. PATENT DOCUMENTS

| | | | |
|---|---|---|---|
| 4,056,635 | 11/1977 | Glen et al. | 424/346 |
| 4,235,892 | 11/1980 | Nagabhushan | 424/226 |
| 4,452,817 | 6/1984 | Glen et al. | 424/346 |
| 4,772,460 | 9/1988 | Malook et al. | 424/10 |
| 4,798,846 | 1/1989 | Glen et al. | 514/731 |
| 5,082,863 | 1/1992 | Apelian et al. | 514/618 |
| 5,637,625 | 6/1997 | Haynes | 514/731 |
| 5,714,520 | 2/1998 | Jones et al. | 514/731 |
| 5,731,355 | 3/1998 | Jones et al. | 514/731 |
| 5,731,356 | 3/1998 | Jones et al. | 514/731 |
| 5,830,907 | 11/1998 | Doble et al. | 514/367 |
| 5,962,536 | 10/1999 | Komer | 514/731 |

FOREIGN PATENT DOCUMENTS

| | | |
|---|---|---|
| 1472793 | 5/1977 | United Kingdom . |

OTHER PUBLICATIONS

Bielen, et al., "The Effect of a Cyclodextrin Vehicle on the Cardiovascular Profile of Propofol in Rats," *Anesthesia Analgesia*, 1996, V. 82, pp. 920–4.

Bretschneider, Herwig, M.D., "Osmolalities of Commercially Supplied Drugs Often Used in Anesthesia," *Anesthesia Analgesia*, 1987, V. 66, pp. 361–2.

Crowther, et al., "Growth of Microorganisms in Propofol, Thiopental, and a 1:1 Mixture of Propofol and Thiopental," *Anesthesia Analgesia*, 1996, V. 82, pp. 475–8.

Doenicke, et al., "A Comparison of Two Formulations for Etomidate, 2–Hydroxypropyl–β–cyclodextrin (HPCD) and Propylene Glycol," *Anesthesia Analgesia*, 1994, V. 79, pp. 933–9.

Doenicke, et al., "Reducing Pain During Propofol Injection: The Role of the Solvent," *Anesthesia Analgesia*, 1996, V. 82, pp. 472–4.

Doenicke. et al., "The New Solvent 2–Hydroxypropyl–8–Cyclodextrin Reduces the Side Effects of Etomidate," *Anesthesiology*, Sep. 1991, . 75, No. 3A, Abstract 381.

Doenicke, et al., "Osmolalities of Propylene Glycol–Containing Drug Formulations for Parenteral Use. Should Propylene Glycol Be Used as a Solvent?," *Anesthesia Analgesia*, 1992, V. 75, pp. 431–5.

Glen, et al., "Pharmacology of an Emulsion Formulation of ICI 35 868," *British Journal of Anaesthesia*, 1984, V. 56, pp. 617–626.

Glen, J.B., "Animal Studies of the Anaesthetic Activity of ICI 35 868," *British Journal of Anaesthesia*, 1980, V. 52, pp. 731–742.

Jones, et al., "Pharmacokinetics of Propofol in Children," *British Journal of Anaesthesia*, 1990, V. 65, pp. 661–667.

Kirk, et al, "Lidocaine Inhibits Growth of Staphylococcus Aureus in Propofol," *Anesthesiology*, Sep. 1992, V. 77, No. 3A, Abstract 407.

Klement, et al., "Pain on I.V. Injection of Some Anaesthetic Agents is Evoked by the Unphysiological Osmolality or pH of Their Formulations," *British Journal of Anaesthesia*, 1991, V. 66, pp. 189–195.

Klement, et al., "Pain on Injection of Propofol: Effects of Concentration and Diluent," *British Journal of Anaesthesia*, 1991, V. 67, pp. 281–284.

McHugh, et al., "Propofol Emulsion and Bacterial Contamination," *Canana Journal of Anaesthesia*, 1995, V. 42, 9/pp. 801–4.

Okell, et al., "Comparison of Arterial and Arterialized Venous Concentrations of Propofol During Infusion of Propofol," *British Journal of Anaesthesia*, 1991, V. 67, pp. 285–288.

Sebel, et al., "Propofol: A New Intravenous Anesthetic," *Anesthesiology*, 1989, V. 71, pp. 260–277.

Stark, R.D., "Propofol ('Diprivan') A New Intravaneous Anaesthetic," *Postgraduate Medical Journal*, 1985, V. 61, Supplement 3, p. 001.

Zoran, et al., "Pharmacokinetics of Propofol in Mixed–breed Dogs and Greyhounds," *American Journal of Veterinary Research.*, May 1993, V. 54, No. 5, pp. 755–760.

"Diprivan," Physicians' Desk Reference®, 50th Ed., pp. 2833–2839. (1991).

"PropoFlow™," Pamplet from Abbott Laboratories, North Chicago, IL 60064, USA, 5 pages. (1991).

"General Requirements for Tests and Assays," The United States Pharmacopeial—The National Formulary, Jan. 1, 1995, 9 pages.

"Liposyn®," Pamplet from Abbott Laboratories, North Chicago, IL, 60064, USA, 2 Pages., (1980).

*Primary Examiner*—Theodore J. Criares
*Assistant Examiner*—Jennifer Kim
*Attorney, Agent, or Firm*—Shook, hardy & Bacon LLP.

[57] ABSTRACT

An anesthetic is provided that includes a mixture of propofol, a tonicity agent, a substantially phospholipid-free emulsifying agent, a preservative such as benzyl alcohol, and water. This anesthetic is made by combining these components and then filtering the mixture of these components through a sterilizing filter. This anesthetic may be parenterally administered to both induce and maintain anesthesia in animals.

2 Claims, No Drawings

PROPOFOL-BASED ANESTHETIC AND METHOD OF MAKING SAME

BACKGROUND OF THE INVENTION

The present invention relates to an anesthetic and a method for making the anesthetic. More specifically, the present invention relates to an anesthetic containing propofol as its active component for use in veterinary applications.

Anesthetics are useful in surgical procedures to artificially produce unconsciousness or to reduce sensitivity to pain. Anesthetics are typically viewed as primarily applicable to humans. However, anesthetics also may be administered to all types of animals to reduce pain when setting broken bones, performing internal surgery, or otherwise handling the animal.

One common method of veterinary anesthetization is to premedicate the animal with an alpha-2 agonist, such as xylazine or detomidine, and then induce anesthesia with ketamine. The ketamine anesthetic may be followed by the administration of a gas anesthetic to maintain anesthesia for the remainder of the procedure. Another common method of veterinary anesthetization is administering a thiobarbiturate mixed with glycerol guaicolate. An anesthesia gas may then be administered to maintain anesthesia for a prolonged surgical procedure.

The primary disadvantage associated with these two methods is that they require access to a gas anesthetic machine. Many surgical procedures take place in remote areas where such a machine is not available. If the inducing agent used to anesthetize is administered throughout the procedure without supplemental gas, recovery is often difficult and could be violent.

Propofol has been used in anesthetic formulations administered to humans and dogs. These propofol formulations contain a phospholipid, such as egg lecithin, which functions as an emulsifying agent. However, phospholipids are good substrates for bacterial growth. Phospholipids are also incompatible with numerous preservatives that are at least somewhat water soluble, such as benzyl alcohol. The addition of such a preservative to a formulation containing phospholipids could destroy the formulation. Without a preservative in the formulation, any excess formulation must be thrown away within a few hours of its first use. Some formulations containing phospholipids also include a chelating or sequestering agent, such as ethylenediaminetetraacetic acid (EDTA). However, EDTA is not truly an antimicrobial substance and, thus, is not as effective as a preservative in preventing microbial growth. Another disadvantage with propofol formulations currently available is that they typically contain relatively small amounts of propofol, generally less than five percent by weight/volume (w/v). Therefore, large quantities of the formulation must be administered to provide the desired anesthetic effect.

To overcome the deficiencies found with conventional anesthetics, an anesthetic formulation containing a preservative and a method for making this anesthetic formulation are needed in the art. In addition, a single anesthetic formulation that can be used to both initially anesthetize an animal and to maintain anesthetization is needed.

SUMMARY OF THE INVENTION

It is therefore an object of the present invention to provide an anesthetic formulation that overcomes these disadvantages.

It is another object of the present invention to provide an effective anesthetic formulation that is compatible with an at least somewhat water soluble preservative so that it may be used multiple times before being thrown away.

It is another object of the present invention to provide an anesthetic that is short acting and has a smooth induction to provide the anesthetized animals with an easy recovery.

It is a further object of the present invention to provide an anesthetic that can be used without supplemental gas so that it can be administered at any location.

Another object of the present invention is to provide an anesthetic that is effective in a short amount of time so that it can be used to induce anesthesia in an animal.

A further object of the present invention is to provide an anesthetic that is safely administered for long periods of time so that it can be administered to maintain anesthetization.

It is another object of the present invention to provide a method for making an anesthetic to achieve the foregoing objects.

According to the present invention, the foregoing and other objects are achieved by an anesthetic that includes of a mixture of propofol, a tonicity agent, a substantially phospholipid-free emulsifying agent, a preservative such as benzyl alcohol, and water. The anesthetic is made by combining these components and then filtering the mixture through a sterilizing filter. The anesthetic may be administered parenterally. The anesthetic may be administered to initially anesthetize and/or to maintain anesthetization.

Additional objects, advantages and novel features of the invention will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF THE PREFERRED EMBODIMENT

The anesthetic of the present invention includes a mixture of propofol, a tonicity agent, an emulsifying agent, a preservative, and water. Propofol (2,6-diisopropylphenol) is the active ingredient for this formulation and functions as the anesthetic. It is a sedative hypnotic agent, which can be used for both the induction and the maintenance of anesthesia. The anesthetic may be parenterally administered to any animal, including humans. It is especially useful for horses, cats and dogs. Most preferably, it is administered to horses.

The emulsifying agent in this mixture acts as a bridge between the oily propofol and the water so as to emulsify the mixture. The emulsifying agent has properties of a surfactant and a solvent. The emulsifying agent allows the present formulation to be injected into animals. The agent is substantially devoid of phospholipids and is nonionic. Preferably, the emulsifying agent used in the formulation of the present invention does not contain phospholipids. Preferably, the emulsifying agent is polyethoxylated castor oil. Polyethoxylated castor oil is a good emulsifier because it is well-tolerated in animals and because it is able to be administered parenterally. Furthermore, it is a chemically stable substance and, unlike phospholipids, it resists oxidation and microbial degradation. One brand of polyethoxylated castor oil that may be used is T-DET C-40, which may be purchased from Harcros Organics, 5200 Speaker Rd., P.O. Box 2930, Kansas City, Kans. 66106-1095.

The tonicity agent of the present invention maintains a substantially isotonic formulation. It functions to make the formulation compatible with animal tissue. It also helps prevent the hemolysis of red blood cells in the animal. The tonicity agent may include, but is not limited to, sodium chloride, potassium chloride, mannitol, glycerin, dextrose, or dextrose anhydrous. Preferably, the tonicity agent is dextrose anhydrous.

The preservative of the present invention functions as an antibacterial or antimicrobial agent. It is at least somewhat soluble in water. Parabens, phenols, and benzyl alcohol are among the preservatives that can be used in the formulation. More specifically, the preservative used in this formulation may include, but is not limited to, benzalkonium chloride, benzethonium chloride, benzoic acid, benzyl alcohol, butyl paraben, cetylpyridinium chloride, chlorobutanol, chlorocresol, cresol, dehydroacetic acid, ethylparaben, methylparaben, methylparaben sodium, phenol, phenylethyl alcohol, potassium benzoate, potassium sorbate, propylparaben, propylparaben sodium, sodium benzoate, sodium dehydroacetate, sodium propionate, sorbic acid, or thymol. Preferably, the preservative is benzyl alcohol. The preservative should meet the Antimicrobial Preservative Effectiveness (APE) test. This test requires cultures of each of the microorganisms, *Aspergillus niger, Staphyloccus aureus, Escherichia coli, Pseudomonas aeruginosa,* and *Candida albicans* to be tested in the formulation. The concentration of viable bacteria in the formulation must be reduced to not more than 0.1% of the initial concentrations by the fourteenth day. The concentrations of viable yeasts and molds must remain at or below the initial concentrations during the first 14 days. The concentration of each test microorganism must remain at or below these designated levels during the remainder of the 28-day test period. The preservative used in this formulation is compatible with the emulsifying agent because a substantially phospholipid-free emulsifying agent is used.

Water functions as a solvent in this formulation. The water used in this anesthetic formulation should be suitable for injection under United States Pharmacopeia (USP) standards. These standards provide that water complying with the U.S. Environmental Protection Agency National Primary Drinking Water Regulations or the comparable regulations of the European Union or Japan be purified by distillation or reverse osmosis. Water, which is suitable for injection according to USP standards, contains no added substances.

The anesthetic of the present invention preferably includes the mixture of about 1–30% w/v propofol, about 1–19.8% w/v tonicity agent, about 5–40% w/v emulsifying agent, and about 0.5–2.5% w/v preservative, if benzoic acid, benzyl alcohol, chlorobutanol, chlorocresol, cresol, dehydroacetic acid, phenol, phenylethyl alcohol, potassium benzoate, potassium sorbate, sodium benzoate, sodium dehydroacetate, sodium propionate, sorbic acid, or thymol is used as the preservative, or about 0.01–0.5% w/v preservative, if benzalkonium chloride, benzethonium chloride, butyl paraben, cetylpyridinium chloride, ethylparaben, methylparaben, methylparaben sodium, propylparaben, or propylparaben sodium is used as the preservative. All percentages are by weight/volume (w/v) unless otherwise noted. The emulsifying agent content varies with the propofol content in a proportional relationship. More preferably, the anesthetic of the present invention includes the mixture of about 9–11% propofol, about 4–8% tonicity agent, about 15–25% emulsifying agent and about 1–2% benzyl alcohol. Most preferably, the anesthetic of the present invention includes the mixture of about 10% of propofol, about 5.4% of dextrose anhydrous, about 20% of polyethoxylated castor oil, and about 1.5% of benzyl alcohol per 100 milliliters of solution wherein a sufficient quantity of water for injection is used to make the balance of the solution.

The anesthetic of the present invention is a substantially isotonic solution, having an osmolarity less than 1. It has a pH between about 5.5 and 9.5.

The anesthetic of the present invention is made by combining propofol, a tonicity agent, an emulsifying agent, a preservative, and water to form a mixture. These components are then mixed for an effective period of time. After these components are thoroughly mixed, the mixture is filtered through a sterilizing filter. The order in which components are added is not critical. Preferably, the remaining water is added last so that a specific quantity of anesthetic may be obtained. This process can be scaled to make any desired quantity of the formulation.

One preferred method of making the anesthetic of the present invention includes placing 30–40% of the water in a vessel, agitating the water, and mixing the tonicity agent with the water until a clear solution forms. Next, an emulsifying agent is mixed with the clear solution until a milky solution forms. Propofol is then mixed with the milky solution for an effective period of time. Typically, it is mixed for at least about 10 minutes. Following this, a preservative is mixed into the solution for an effective period of time. Typically, it is mixed for at least about 10 minutes. Agitation is discontinued, and the balance of the water is added to the solution. The anesthetic formulation is then mixed for an effective period of time. Generally, it is mixed for at least about 10 minutes. Next, it is filtered through a sterilizing filter. Preferably, the anesthetic is filtered through a 0.22 micron or smaller absolute sterilizing filter, wherein the filter contributes to the emulsification process. Most preferably, this filter is made of polytetrafluoroethylene. A desirable polytetrafluoroethylene 0.22 micron absolute sterilizing filter may be purchased from Millipore Corporation, 80 Ashby Road, Bedford, Mass. 01730.

The following are examples of methods for making the propofol-based anesthetics of this invention. These examples do not limit the scope of this invention.

EXAMPLE 1

40 milliliters of water for injection, USP, were added to a glass vessel. Agitation began. With continued agitation, 5.4 grams of dextrose anhydrous, USP, were added to the water and mixed with the water until the dextrose anhydrous dissolved and a clear solution formed. With continued agitation, 20 grams of T-DET C-40 polyethoxylated castor oil were added to the mixture and mixed until a milky solution formed. With continued agitation, 10 grams of propofol were added to the solution and mixed with it for over 10 minutes. With continued agitation, 1.5 grams of benzyl alcohol were added to the mixture and mixed for over 10 minutes. Agitation was discontinued and the solution was diluted to a volume of 100 milliliters with water for injection, USP. Agitation was restarted, and the solution was mixed for over 10 minutes. With continued agitation, the solution was filtered through a 0.22 micron absolute sterilizing filter into sterile containers, and it was sealed with appropriate sterile closures. This formulation had an osmolarity of 0.273 and a pH of 7.55.

EXAMPLE 2

35 milliliters of water for injection, USP, are added to a suitable stainless steel vessel. Agitation begins. With continued agitation, 5 grams of potassium chloride are added to the water and mixed with the water until the potassium chloride dissolves and a clear solution forms. With continued agitation, 32 grams of polyethoxylated castor oil are added to the mixture and mixed until a milky solution forms. With continued agitation, 25 grams of propofol are added to the solution and mixed with it for 10 minutes. With continued agitation, 90 milligrams of methylparaben and 10 milligrams of propylparaben are added to the mixture and mixed for 10 minutes (or until dissolved). Agitation is discontinued, and the solution is diluted to a volume of 100 milliliters with water for injection, USP. Agitation is restarted, and the solution is mixed for 10 minutes. With continued agitation, the solution is filtered through a suitable sterilizing filter into sterile containers and sealed with appropriate sterile closures.

EXAMPLE 3

30 milliliters of water for injection, USP, are added to a glass vessel. Agitation begins. With continued agitation, 15 grams of mannitol are added to the water and mixed with the water until the mannitol dissolves and a clear solution forms. With continued agitation, 40 grams of polyethoxylated castor oil are added to the mixture and mixed until a milky solution forms. With continued agitation, 30 grams of propofol are added to the solution and mixed with it for 15 minutes. With continued agitation, 1.25 grams of chlorobutanol are added to the mixture and mixed for 20 minutes. Agitation is discontinued, and the solution is diluted to a volume of 100 milliliters with water for injection, USP. Agitation is restarted, and the solution is mixed for 10 minutes. With continued agitation, the solution is filtered through a suitable sterilizing filter into sterile containers and sealed with appropriate sterile closures.

EXAMPLE 4

40 milliliters of water for injection, USP, are added to a suitable stainless steel vessel. Agitation begins. With continued agitation, 19 grams of glycerin are added to the water and mixed with the water until the glycerin dissolves and a clear solution forms. With continued agitation, 5 grams of polyethoxylated castor oil are added to the mixture and mixed until a milky solution forms. With continued agitation, 2 grams of propofol are added to the solution and mixed with it for 10 minutes. With continued agitation, 1.5 grams of potassium sorbate are added to the mixture and mixed for 10 minutes. Agitation is discontinued, and the solution is diluted to a volume of 100 milliliters with water for injection, USP. Agitation is restarted, and the solution is mixed for 10 minutes. With continued agitation, the solution is filtered through a suitable sterilizing filter into sterile containers and sealed with appropriate sterile closures.

EXAMPLE 5

32 milliliters of water for injection, USP, are added to a suitable stainless steel vessel. Agitation begins. With continued agitation, 2 grams of dextrose anhydrous, USP, is added to the water and mixed with the water until the dextrose anhydrous dissolves and a clear solution forms. With continued agitation, 20 grams of polyethoxylated castor oil are added to the mixture and mixed until a milky solution forms. With continued agitation, 25 grams of propofol are added to the solution and mixed with it for 25 minutes. With continued agitation, 0.5 grams of phenol are added to the mixture and mixed for 30 minutes. Agitation is discontinued, and the solution is diluted to a volume of 100 milliliters with water for injection, USP. Agitation is restarted, and the solution is mixed for 30 minutes. With continued agitation, the solution is filtered through a suitable sterilizing filter into sterile containers and sealed with appropriate sterile closures.

EXAMPLE 6

37 milliliters of water for injection, USP, are added to a glass vessel. Agitation begins. With continued agitation, 10 grams of sodium chloride are added to the water and mixed with the water until the sodium chloride dissolves and a clear solution forms. With continued agitation, 25 grams of polyethoxylated castor oil are added to the mixture and mixed until a milky solution forms. With continued agitation, 20 grams of propofol are added to the solution and mixed with it for 11 minutes. With continued agitation, 1 gram of benzyl alcohol is added to the mixture and mixed for 12 minutes. Agitation is discontinued, and the solution is diluted to a volume of 100 milliliters with water for injection, USP. Agitation is restarted, and the solution is mixed for 10 minutes. With continued agitation, the solution is filtered through a suitable sterilizing filter into sterile containers and sealed with appropriate sterile closures.

The anesthetic of the present invention is effective in a short amount of time, thus making it an effective anesthetic to be used for induction of anesthesia. In addition, the anesthetic of the present invention can be safely administered for long periods of time, thus making it an effective anesthetic for maintaining anesthesia. In one embodiment of the invention, the anesthetic is parenterally administered not only to induce anesthesia but to maintain anesthesia as well. Preferably, the anesthetic is initially administered in a quantity of approximately of 2.0 milligrams per kilogram body weight of the animal (mg/kg). Then, if anesthetization is continued using this anesthetic for a long period of time, the amount of anesthetic can then be decreased to approximately 0.2 milligrams per kilogram body weight of animal per minute (mg/kg/min). Because this anesthetic formulation can be used to maintain anesthesia in addition to inducing anesthesia, it is particularly convenient to use. The user does not have to change to another anesthetic and does not need to switch to a bulky gas anesthesia machine during a procedure.

The propofol-based anesthetic of the present invention is short-acting and has a smooth induction. Once administration of this anesthetic is stopped, it has a short term effect. Thus, the animal has a quick and smooth recovery. Full recovery can be observed in a matter of minutes.

It is believed the anesthetic of the present invention will have a shelf life that is greater than about 3 years when it is stored in sealed containers. Tests have proven that the formulation of the present invention does not lose efficacy when stored for over 6 months.

From the foregoing, it will be seen that this invention is one that is well adapted to attain all the ends and objects hereinabove set forth together with other advantages which are obvious and inherent to the formulation. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth is to be interpreted as illustrative and not in a limited sense.

I claim:

1. An anesthetic, comprising the mixture of:
about 1–30% propofol;
about 1–19.8% tonicity agent;
about 5–40% phospholipid-free emulsifying agent;
about 0.5–2.5% benzyl alcohol; and
water.

2. An anesthetic, comprising the mixture of:
about 9–11% propofol;
about 4–8% tonicity agent;
about 15–25% phospholipid-free emulsifying agent;
about 1–2% benzyl alcohol; and
water.

* * * * *